United States Patent [19]

Takahasi

[11] Patent Number: 4,537,510

[45] Date of Patent: Aug. 27, 1985

[54] OUTPUT CONTROL DEVICE FOR LIGHT DETECTORS FOR PHOTOMETERS

[75] Inventor: Kenichiro Takahasi, Naka, Japan

[73] Assignee: Hitachi, Ltd., Tokyo, Japan

[21] Appl. No.: 448,271

[22] Filed: Dec. 9, 1982

[30] Foreign Application Priority Data

Dec. 15, 1981 [JP] Japan .................. 56-203249

[51] Int. Cl.$^3$ ............................ G01J 1/16; G01J 1/18
[52] U.S. Cl. .................. 356/435; 356/229; 356/230; 356/433; 250/214 AG; 250/565
[58] Field of Search ........... 356/435, 434, 433, 436, 356/222, 226, 229, 230, 438, 439, 440, 441, 442; 250/565, 214 AG

[56] References Cited

U.S. PATENT DOCUMENTS

| | | | |
|---|---|---|---|
| 3,071,037 | 1/1963 | Brumley | 250/565 |
| 3,698,820 | 10/1972 | Hanff et al. | 356/435 |
| 3,746,452 | 7/1973 | Teboul et al. | 356/438 |
| 4,095,098 | 6/1978 | Looper | 356/435 |
| 4,127,813 | 11/1978 | Hiroshima et al. | 250/214 AG |

Primary Examiner—R. A. Rosenberger
Assistant Examiner—Michael F. Vollero
Attorney, Agent, or Firm—Antonelli, Terry & Wands

[57] ABSTRACT

Apparatus for controlling output signals from two light detectors in a photometer. The sensitivities of the light detectors, or the gains in amplifiers for amplifying output signals from the light detectors are controlled in such a manner that the sensitivity characteristics and output characteristics of the two light detectors are in agreement with one another, to thereby improve the measuring accuracy thereof.

14 Claims, 4 Drawing Figures

OUTPUT CONTROL DEVICE FOR LIGHT DETECTORS FOR PHOTOMETERS

BACKGROUND OF THE INVENTION

This invention relates to a measuring circuit of a double beam or 2-wave-length system for photometers, which utilize the light from a single light source, and more particularly to a device for correcting the sensitivities of two light detectors, which are used to detect the light passing through an object sample and the light passing through a reference sample, in such a manner that the sensitivities of these detectors become equal to each other.

In order to determine the absorbance of an object sample by a photometer, a device for applying the light to an object sample and a reference sample, detecting the light passing through these samples, by a plurality of detecting means, i.e. a plurality of light detectors, and determining a ratio of levels of signals detected thereby is widely used. What is important for such a photometer is to set the sensitivities of a light detector for an object sample and a light detector for a reference sample to the same level. When the sensitivities of these light detectors are different, the measurement values of transmissivities and absorbances of samples become different; measurement errors occur. Accordingly, when a plurality of light detectors are used together, it is necessary that the light detectors have the closest possible characteristics. However, it is impossible to obtain light detectors having completely the same temperature characteristics and completely the same wave-length and sensitivity characteristics. Therefore, when an ambient temperature varies, or when a measuring wave-length is changed by passing the light through spectroscopes or filters, measurement errors occur.

In a conventional photometer, the light from a single light source is subjected to a time division system to alternately detect the light passing through an object sample and the light passing through a reference sample, and thereby eliminate the drawbacks encountered in the above-described photometer utilizing a plurality of light detectors. However, such a conventional photometer using a time division system also has problems peculiar thereto. Namely, in a time division system, the time, during which signals can be obtained, is reduced to more than half, and only such signals that correspond to different instants can be obtained. This tends to cause a decrease in the measuring accuracy. When signals include noise having a frequency close to a time division frequency, beat occurs. When signals include noise having a frequency higher than a time division frequency, the responding capability thereof lowers, and it becomes difficult to eliminate a noise component. A conventional photometer employing a time division system has many drawbacks mentioned above. In a time division system, a chopper is used. Since a rotational speed of a chopper is limited, a phenomenon varying at a high speed cannot be measured faithfully. Especially, in an atomic absorption analyzer lately developed, the high-speed atomization is carried out, and a time division system does not actually serve the purpose.

SUMMARY OF THE INVENTION

An object of the present invention is to provide a photometer having a comparatively simple construction and a high measuring accuracy.

Another object of the present invention is to provide a 2-wave-length spectrophotometer or a double beam spectrophotometer, which permits relatively correcting the sensitivities of two light detectors in use, and thereby improving the measuring accuracy thereof to a great extent.

Still another object of the present invention is to provide a photometer capable of measuring at a high accuracy even a phenomenon varying at a high speed.

A further object of the present invention is to provide a photometer using two light detectors consisting of two semiconductor light detectors, the sensitivity characteristics of which can be corrected easily.

A further object of the present invention is to provide a photometer having a high S/N ratio.

In order to achieve the above objects, the present invention provides a photometer comprising a reference light source adapted to emit the modulated light of a predetermined frequency to a light detector for receiving the light passing through an object sample and a light detector for receiving the light passing through a reference sample, two filter circuits adapted to detect such components of output signals from the two light detectors that represent the modulated light from the reference light source, and a correcting and computing element or a computing control element for correcting the relative sensitivities of the two light detectors.

The present invention further provides a photometer, which is similar to the photometer described above, and which includes a circuit for controlling the luminance of the reference light source in accordance with a level of an output signal from the light detector for the reference sample.

The present invention further provides a photometer, which is similar to the photometers described above, and which includes two semiconductor light detectors, and gain-variable amplifiers adapted to amplify output signals from the light detectors, the gains in these amplifiers being controlled by an output signal from the correcting and computing element to correct the relative sensitivities of the two light detectors.

DESCRIPTION OF THE PREFERRED EMBODIMENTS

Figure 1A:
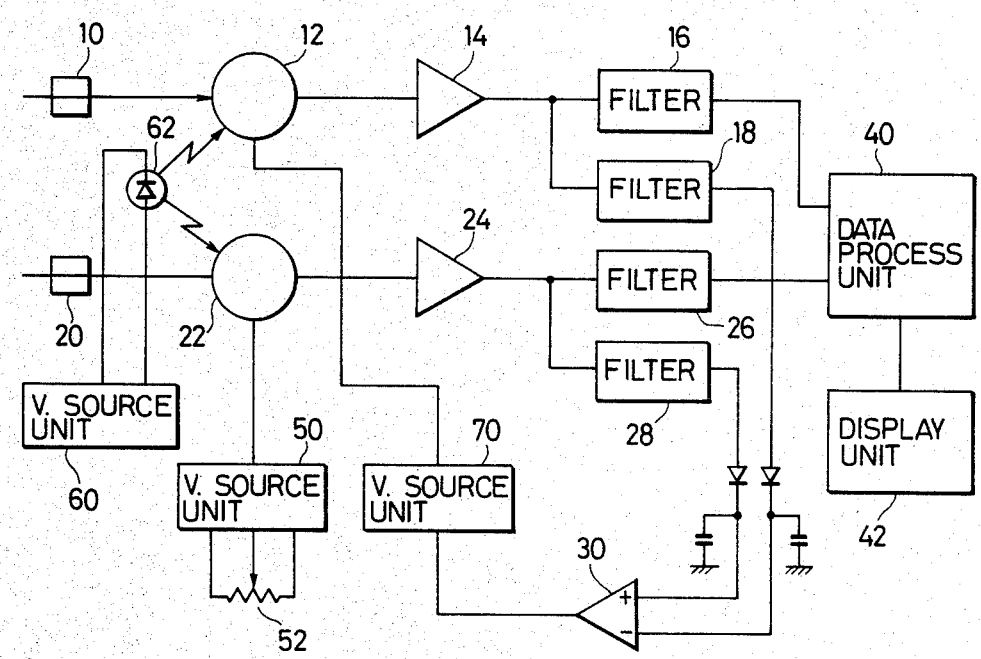
FIGS. 1A and 1B are block diagrams of circuits for correcting the sensitivities of light detectors in photometers embodying the present invention.

Referring to FIG. 1A, the light passing through a sample cell 10 is detected by a photomultiplier 12. Also, the light passing through a reference sample cell 20 is detected by a photomultiplier 22. The modulated light having a predetermined frequency is applied to the photomultipliers 12, 22 from a reference light source 62. The reference light source 62 used in this embodiment consists of a light-emitting diode, which may be substituted by some other light-emitting element, for example, a heavy hydrogen discharge tube. Reference numeral 60 denotes a power source for the reference light source 62. Output signals from the photomultipliers 12, 22, which have thus detected the light passing through the cells 10, 20 and the modulated light from the reference light source 62, are amplified by amplifiers 14, 24, respectively, to be supplied to filter circuits 16, 18 on the side of the sample cell 10 and filter circuits 26, 28 on the side of the reference sample cell 20. Each of the filter circuits consists of a band-pass filter. The filter circuit 16 is adapted to pass therethrough a signal representative of the light passing through the sample cell 10, and the filter circuit 18 to detect only such a component of an output signal from the photomultiplier 12 that is representative of the modulated light from the reference light source 62. Also, the filter circuit 26 is adapted to pass therethrough a signal representative of the light passing through the reference sample cell 20, and the filter circuit 28 to detect only such a component of an output signal from the photomultiplier 22 that is representative of the modulated light from the reference light source 62. A data processing unit 40 is adapted to receive a signal, which is representative of the object sample, from the filter circuit 16, and a signal, which is representative of the reference sample, from the filter circuit 26, carry out the computation of the signals, and output a signal representative of a measurement value, which is indicated on a display unit 42. When the sensitivities of the photomultipliers 12, 22 are different, a measurement value including an error would be obtained. The sensitivities of the photomultipliers 12, 22 are reflected in an output signal from the filter circuit 18, which is on the side of the object sample, and which is adapted to detect such a component of an output signal from the photomultiplier 12 on the side of the object sample that is representative of the modulated light from the reference light source 62, and an output signal from the filter circuit 28, which is on the side of the reference sample, and which is adapted to detect such a component of an output signal from the photomultiplier 22 on the side of the reference sample that is representative of the modulated light from the reference light source 62. Namely, when there is a difference between the sensitivities of the two photomultipliers 12, 22, which receive the light from the sole reference light source 62, output signals from the filter circuit 18 on the side of the object sample and the filter circuit 28 on the side of the reference sample have different values. A difference between the values of output signals from the filter circuits 18, 28 can be regarded as a difference between the sensitivities of the multipliers 12, 22. When output signals from the filter circuits 18, 28 are inputted into a subtracter 30 to carry out subtraction, a signal representative of a difference between the sensitivities of the photomultipliers 12, 22 is outputted therefrom. This output signal from the subtracter 30 is applied to a voltage source unit 70 for the photomultiplier 12 to control an output voltage therefrom and the sensitivity of the photomultiplier. When, for example, the sensitivity of the photomultiplier 12 on the side of the object sample is higher than that of the photomultiplier 22 on the side of the reference sample, a negative voltage is outputted from the subtracter 30 to control the voltage source unit 70 in such a manner that the sensitivity of the photomultiplier 12 is reduced. Conversely, when the sensitivity of the photomultiplier 12 is lower than that of the photomultiplier 22, a positive voltage is outputted from the subtractor to control the voltage source unit 70 in such a manner that the sensitivity of the photomultiplier 12 is increased. Accordingly, the sensitivity of the photomultiplier 12 on the side of the object sample is controlled automatically so as to become equal to that of the photomultiplier 22 on the side of the reference sample. An applied voltage for the photomultiplier 22 on the side of the reference sample is regulated by a variable resistor 52, which is provided in a power source 50, to set the photomultiplier 12 for the object sample to optimum sensitivity conditions.

Figure 1B:
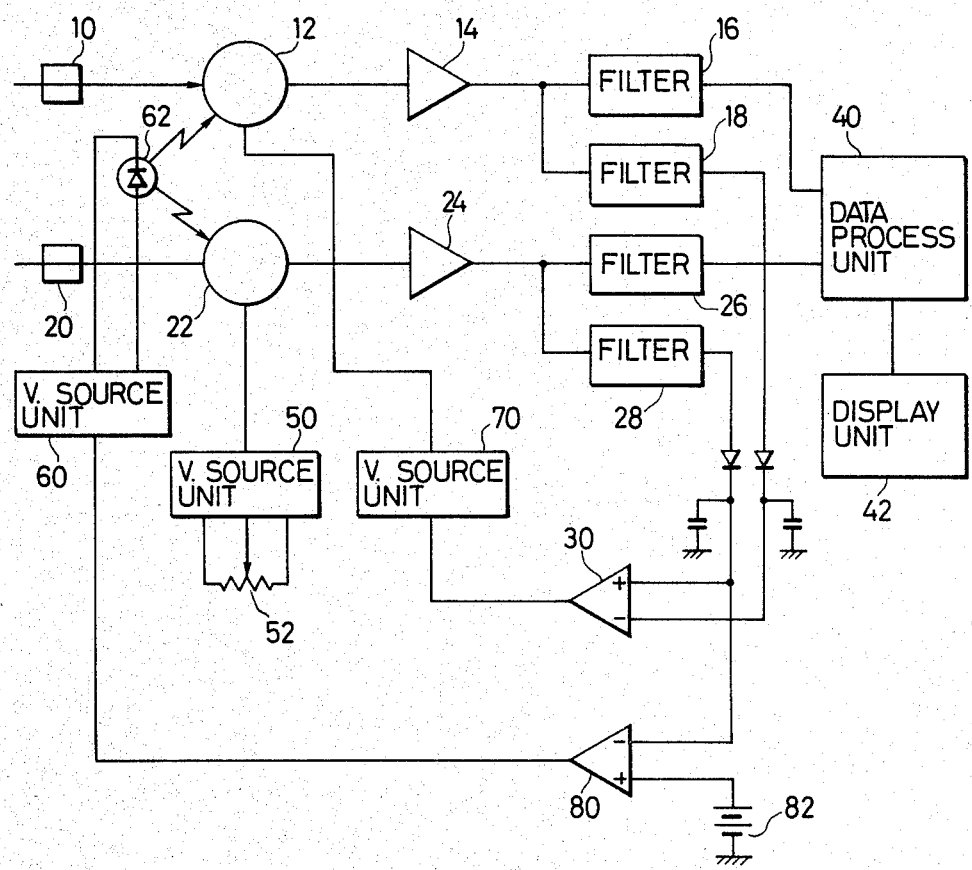

Another embodiment of the present invention shown in FIG. 1B will be described. The construction of a circuit for correcting the output sensitivities of two photomultipliers in this embodiment is identical with that of the corresponding circuit in the embodiment shown in FIG. 1A. FIG. 1A. The same constructional elements of the embodiments shown in FIGS. 1B and 1A are designated by the same reference numerals. In the embodiment shown in FIG. 1B, the illuminance of a reference light source 62 is controlled automatically to correct the sensitivities of the photomultipliers more effectively. A voltage of an output signal from a filter circuit 28 on the side of a reference sample is compared with a predetermined reference voltage 82 in a subtracter 80. An output voltage at a power source 60 for a reference light source 62 is regulated by an output signal from the subtracter 80 to thereby control the luminance of the reference light source 62. For example, when the sensitivity of a photomultiplier 22 on the side of the reference sample increases, so that an output voltage at a filter circuit 28 becomes higher than an electric potential of the reference voltage 82, a negative voltage is outputted from the subtracter 80 to control an output voltage at the power source 60 in such a manner that the illuminance of the reference light source 62 is reduced. When the sensitivity of the photomultiplier 22 lowers, so that an output voltage at the filter circuit 28 becomes lower than the reference voltage 82, a positive voltage is outputted from the subtracter 80 to control an output voltage at the power source 60 in such a manner that the illuminance of the reference light source 62 is increased. The illuminance of the reference light source 62 is thus controlled to be kept at a constant level.

In the two embodiments described above, photomultipliers are used, the light-receiving sensitivities of which can be controlled by an applied voltage. Some other embodiments employing light detectors, the light-receiving sensitivities of which cannot be controlled by an applied voltage, will now be described in connection with a method of correcting the sensitivities thereof.

Figure 2A:
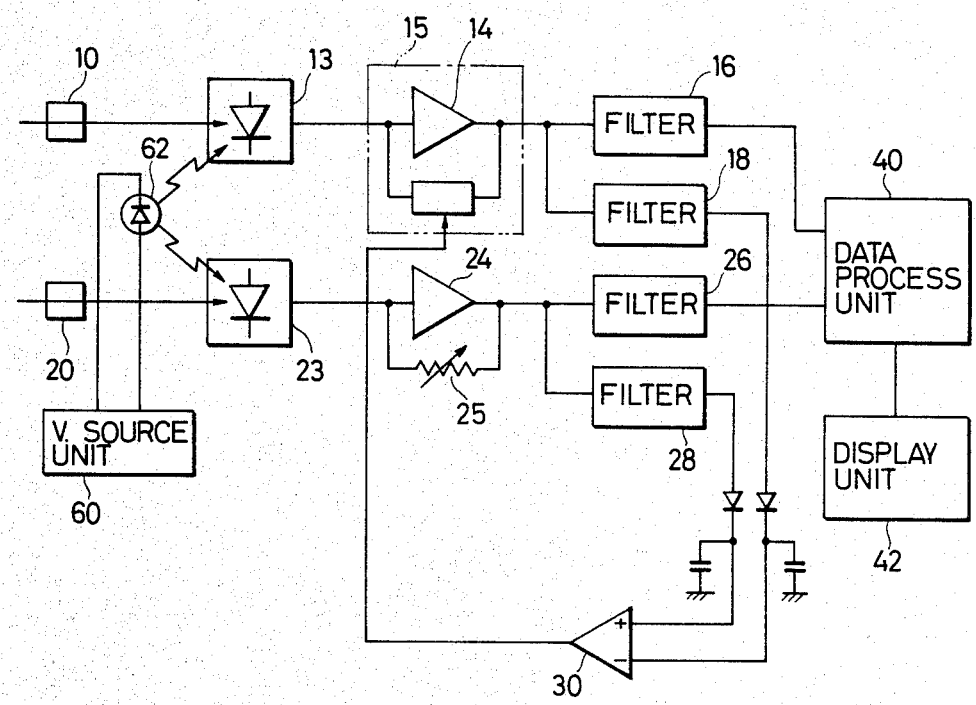
FIGS. 2A and 2B are block diagrams of circuits for correcting the sensitivities of semiconductor light detectors in photometers of further embodiments of the present invention.

FIG. 2A illustrates an embodiment using two semiconductor light detectors. The light passing through a sample cell 10 is detected by a semiconductor light detector 13, and the light passing through a reference sample cell 20 by a semiconductor light detector 23. Output signals from the semiconductor light detectors 13, 23 are amplified by gain-variable amplifiers 15, 24. Filter circuits 16, 18, 26, 28 have the same functions as the filter circuits in the embodiment shown in FIG. 1A. An output terminal of a subtracter 30 is connected to a gain-variable terminal of the gain-variable amplifier 15. When the sensitivity of the semiconductor light detector 13 on the side of an object sample is higher than that of the semiconductor light detector 23 on the side of a reference sample, a negative voltage is outputted from the subtracter 30 by the same operation as described previously, to reduce the gain in an amplifier 14. In a contrary case, the gain in the amplifier 14 is increased by an output from the subtracter 30. Namely, when the sensitivities of the two semiconductor light detectors 13, 23 are different as mentioned above, the amplification degree of an output from the semiconductor light detector 13 is controlled on the basis of the sensitivity of the semiconductor light detector on the side of the reference sample. An output from the semiconductor light detector 23 on the side of the reference sample is controlled by a variable resistor 25 provided in the amplifier 24, to set the semiconductor light detector 13 on the side of the object sample to optimum sensitivity condition.

Figure 2B:
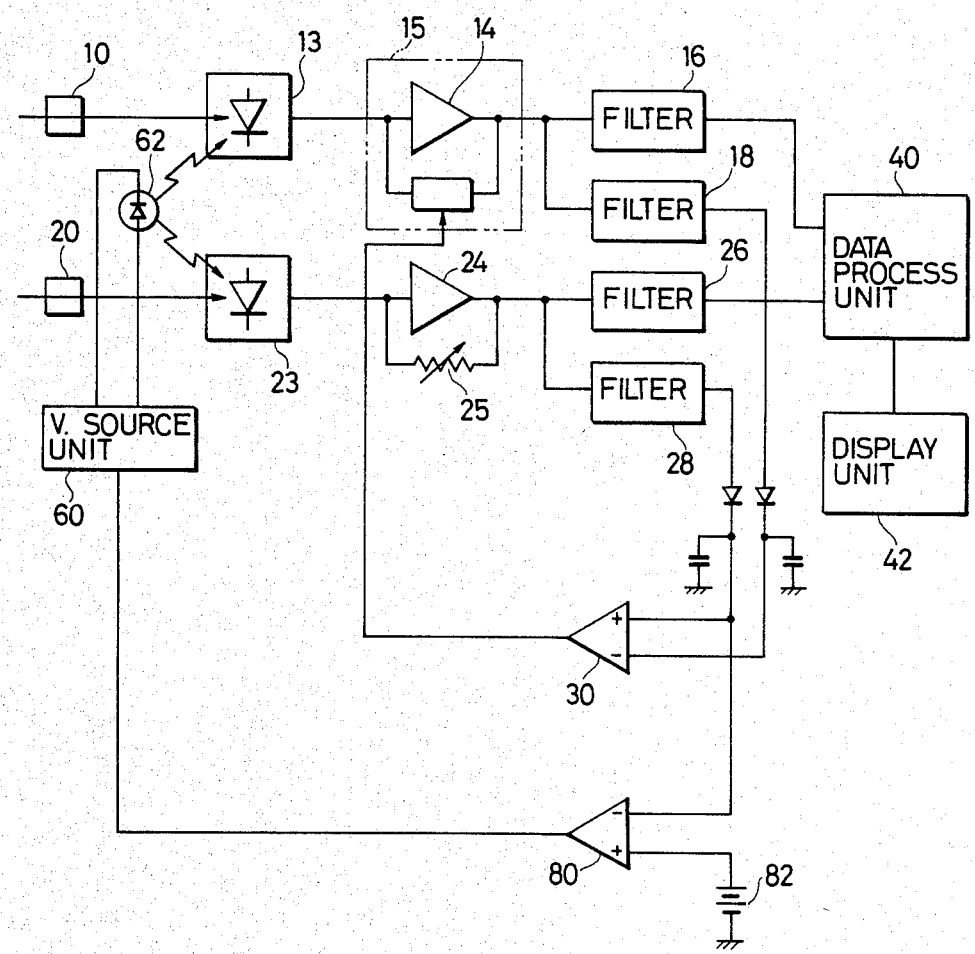

An embodiment shown in FIG. 2B is the same as the embodiment shown in FIG. 2A, which employs semiconductor light detectors, except that the same circuit as shown in FIG. 1B, for automatically controlling a reference light source 62 is added thereto. The construction and operation of the embodiment shown in FIG. 2B are the same as those of the embodiment shown in FIG. 1B, and therefore, a description thereof will be omitted. The embodiments shown in FIGS. 2A and 2B employ semiconductor light detectors. Even when these semiconductor light detectors are substituted by photoconductive cells with the construction of the embodiment as a whole left unchanged, the embodiment can be operated in the same manner.

In the above four embodiments, photometers, in which the sensitivities of the light detectors on the side of the object samples are controlled on the basis of that of the light detectors on the side of the reference samples, are described. On the contrary, even when these embodiments are set in such a manner that the sensitivities of the light detectors on the side of the reference samples are controlled on the basis of that of the light detectors on the side of the object samples with the construction of the embodiments left unchanged, the objects of the invention can be achieved.

According to the present invention described above, the sensitivity characteristics of the light detectors and the gains in the amplifiers in a double beam photometer are corrected automatically, so that a measurement error due to a difference between the sensitivities of the light detectors can be corrected.

Therefore, the drawbacks encountered in a conventional double beam spectrophotometer can be eliminated, and, even when the measuring conditions including the temperature vary, an analytical curve once prepared can be used. This allows the accuracy of measurement and analysis by the photometer to be improved to a great extent.

A photometer of this system was experimentally made to determine the characteristics thereof. The results show that this photometer has the following effects as compared with a conventional photometer of a time division system. (1) The S/N ratio increases about ten times that of a conventional photometer of a time division system.

(2) A conventional photometer of a time division system has a mechanical limitation on the number of rotations per minute of a chopper motor. In the photometer of the system according to the present invention, the responding capability thereof with respect to a quickly-varying phenomenon can be improved around several ten times.

(3) A mechanical chopper is not required, so that the photometer has a simpler construction and can be made at a lower cost. Moreover, the reliability of the operation of the photometer can be improved.

The system according to the present invention can also be applied to a photometer of a two-wavelength system shown in FIG. 2.

The photometer according to the present invention can be obtained by making comparatively simple improvements on a conventional photometer, i.e. by providing a conventional photometer with a means for applying the modulated light from the reference light source to the light detector on the side of an object sample and the light detector on the side of a reference sample to compare the outputs from the light detectors and automatically detect and correct the difference between the sensitivities thereof. The photometer permits improving the measuring accuracy thereof to a great extent.

What is claimed is:

1. A device for correcting outputs from light detectors for photometers, comprising a first light detector adapted to detect the light passing through an object sample, a second light detector adapted to detect the light passing through a reference sample, a reference light source adapted to apply modulated light having a predetermined frequency to said first and second light detectors, a first filter circuit adapted to detect such a component of an output signal from said first light detector that is representative of the modulated light from said reference light source, a second filter circuit adapted to detect such a component of an output signal from said second light detector that is representative of the modulated light from said reference light source, and a correcting and computing means adapted to compare output signals from said first and second filter circuit and to correct the relative sensitivities of said first and second light detectors in accordance with the results of the comparison.

2. A device for correcting outputs from light detectors according to claim 1, wherein said correction and computing means comprises a subtracter adapted to compare output signals from said first and second filter circuits and to correct the sensitivity of said first light detector.

3. A device for correcting outputs from light detectors according to claim 1, wherein said correcting and computing means continuously corrects the relative sensitivities of said first and second light detectors while said first and second light detectors detect the light passing through the object sample and the reference sample, respectively, and provide outputs indicative thereof.

4. A device for correcting outputs from light detector adapted to detect the light passing through an object sample, a second light detectors for photometers, comprising a first light detector adapted to detect the light passing through a reference sample, a reference light source adapted to apply modulated light having a predetermined frequency to said first and second light detectors, a first filter circuit adapted to detect such a component of an output signal from said first light detector that is representative of the modulated light from said reference light source, a second filter circuit adapted to detect such a component of an output signal from said second light detector that is representative of the modulated light from said reference light source, a correcting and computing means adapted to compare output signals from said first and second filter circuits and to correct the relative sensitivities of said first and second light detectors in accordance with the results of the comparison, and a means for comparing a voltage of an output signal of one of said first and second filter circuits with a predetermined reference voltage to control the illuminance of said reference light source in accordance with the result of the comparison.

5. A device for correcting outputs from light detectors for photometers according to claim 4, wherein said correcting and computing means comprises a subtractor adapted to compare output signals from said first and second filter circuits and to correct the sensitivity of said first light detector by an output signal therefrom.

6. A device for correcting outputs from light detectors according to claim 4, wherein said correcting and computing means continuously corrects the relative sensitivities of said first and second light detectors while said first and second light detectors detect the light passing through the object sample and the reference sample, respectively, and provide outputs indicative thereof.

7. A device for correcting outputs from light detectors for photometers, comprising a first light detector adapted to detect the light passing through an object sample, a second light detector adapted to detect the light passing through a reference sample, a reference light source adapted to apply modulated light having a predetermined frequency to said first and second light detectors, a gain-variable amplifier adapted to amplify an output signal from said first light detector, a first filter circuit adapted to detect such a component of an output signal from said gain-variable amplifier that is representative of the modulated light from said reference ligh source, a second filter circuit adapted to detect such a component of an output signal from said second light detector that is representative of the modulated light from said reference light source, and a computing and controlling means adapted to compare output signals from said first and second filter circuits to control the gain in said gain-variable amplifier in accordance with the result of the comparison.

8. A device for correcting outputs from light detectors for photometers according to claim 7, wherein said computing and controlling means comprises a subtracter adapted to compare output signals from said first and second filter circuits and to control the gain in said gain-variable amplifier.

9. A device for correcting outputs from light detectors for photometers according to claim 7, wherein said light detectors consist of semiconductor light detectors.

10. A device for correcting outputs from light detectors according to claim 7, wherein said computing and controlling means continuously controls the gain in said gain-variable amplifier while said first and second light detectors detect the light passing through the object sample and the reference sample, respectively, and provide outputs indicative thereof.

11. A device for correcting outputs from light detectors for photometers, comprising a first light detector adapted to detect the light passing through an object sample, a second light detector adapted to detect the light passing through a reference sample, a reference light source adapted to apply modulated light having a predetermined frequency to said first and second light detectors, a gain-variable amplifier adapted to amplify an output signal from said first light detector, a first filter circuit adapted to detect such a component of an output signal from said gain-variable amplifier that is representative of the modulated light from said reference light source, a second filter circuit adapted to detect such a component of an output signal from said second light detector that is representative of the modulated light from said reference light source, a computing and controlling means adapted to compare output signals from said first and second filter circuits and to control the gain in said gain-variable amplifier in accordance with the result of the comparison, and a control means adapted to compare an output signal from said second filter circuit with a predetermined reference value and control the illuminance of said reference light source in accordance with the result of the comparison.

12. A device for correcting outputs from light detectors for photometers according to claim 11, said computing and controlling means comprises a subtractor adapted to compare output signals from said first and second filter circuits and to control the gain in said gain-variable amplifier.

13. A device for correcting outputs from light detectors for photometers according claim 11, wherein said light detectors consist of semiconductor light detectors.

14. A device for correcting outputs from light detectors according to claim 11, wherein said computing and controlling means continuously controls the gain in said gain-variable amplifier while said first and second light detectors detect the light passing through the object sample and the reference sample, respectively, and provide outputs indicative thereof.

* * * * *